(12) United States Patent
O'Lenick

(10) Patent No.: US 9,045,593 B1
(45) Date of Patent: Jun. 2, 2015

(54) SILICONE POLYMERS CONTAINING UV PHOTOSTABILIZING GROUPS

(71) Applicant: Thomas George O'Lenick, Dacula, GA (US)

(72) Inventor: Thomas George O'Lenick, Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 0 days.

(21) Appl. No.: 14/120,763

(22) Filed: Jun. 25, 2014

Related U.S. Application Data

(60) Provisional application No. 61/967,745, filed on Mar. 26, 2014.

(51) Int. Cl.
| | |
|---|---|
| *C08G 77/16* | (2006.01) |
| *C08G 63/695* | (2006.01) |
| *C07D 251/54* | (2006.01) |
| *C08G 77/46* | (2006.01) |
| *C08G 77/04* | (2006.01) |

(52) U.S. Cl.
CPC .............. *C08G 63/695* (2013.01); *C07D 251/54* (2013.01); *C08G 77/46* (2013.01); *C08G 77/045* (2013.01)

(58) Field of Classification Search
CPC ...... C08G 77/46; C08G 77/045; C07D 251/54
USPC .......................................................... 528/26
See application file for complete search history.

(56) References Cited

U.S. PATENT DOCUMENTS

| | | | |
|---|---|---|---|
| 7,915,330 B2 | 3/2011 | Bonda et al. | |
| 2013/0280190 A1 * | 10/2013 | Maestri et al. | ................. 424/60 |

* cited by examiner

*Primary Examiner* — Kuo-Liang Peng

(57) ABSTRACT

The present invention is directed to a series of silicone containing polymers that contain photostabilizers that act as photo stabilizers for Ultra Violet radiation. The polymers of the present invention are multi functional sun screening additives that allow in addition to photostabilizing the active sunscreen agent found in sunscreens, additionally provide high levels of UV protection in a cosmetically elegant base. The photostabilizing compositions are derived from a tricarboxylic triazine compound.

17 Claims, No Drawings

SILICONE POLYMERS CONTAINING UV PHOTOSTABILIZING GROUPS

RELATED APPLICATIONS

This application claims priority to and benefit of U.S. Provisional Application Nos. 61/967,745, filed Mar. 26, 2014, the disclosures of each of which are incorporated herein for all purposes.

FIELD OF THE INVENTION

The present invention is directed to a series of silicone containing polymers that contain photostabilizers that act as photo stabilizers for Ultra Violet radiation. The polymers of the present invention are multi functional sun screening additives that allow in addition to photostabilizing the active sunscreen agent found in sunscreens, additionally provide high levels of UV protection in a cosmetically elegant base.

BACKGROUND OF THE INVENTION

The formulation of a high performance sunscreen product requires many ingredients. Most important of which is the sunscreen active. Since sunscreens are considered by the Food and Drug Administration (FDA) as a drug, the actives that can be used are carefully regulated. Some of these materials do however experience photodegradation in formulation. It is the minimization of this type photodegradation issues that the present invention is directed.

Ultraviolet radiation from the sun or artificial sources can damage materials and/or coatings containing photoactive substances, such as photoactive polymers, pigments and dyes, by altering chemical bonds in the structure of the polymer, pigment, or dye. This photodegradation can lead to color fading, loss of gloss, and/or loss of physical and protective properties of a photodegradable or photoactive polymer or coating. Understandably, photostabilizing or photostabilization is the process or effect of preventing the photodegradation of photoactive substances. In particular, photostabilizing can be increasing the light fastness of a composition, preventing yellowing, or color formation, and delaying or preventing photochemical reactions that adversely affect photoactive substances.

One method to protect photoactive substances is through the use of UV filters; one class of materials particularly suited to act as a UV filters are naphthalate polyesters, for example those patented by this assignee. Naphthalate polyesters are suitable UV filters because they have very high extinction coefficients and subsequently low transmission of ultraviolet (UV) radiation. Additionally, the incorporation of naphthalates into polyester polymers increase the polymer's thermal and structural stability, decrease the polymer's gas permeability, and dramatically block the transmission of UV radiation through the polymer. The UV filtering and improved physical characteristics have led to the use of naphthalate polymers and blends in a wide range of applications including beverage and personal care product packaging, protective screening films, sail cloth fiber and as an additive stabilizer in sunscreens and cosmetics.

While efficiently absorbing UV radiation, naphthalates dissipate (emit) the absorbed energy through fluorescence. Fluorescence is a type of luminescence in which an atom or molecule emits radiation, i.e., a photon, in passing from a higher to a lower electron state, as described in my co-pending application Ser. No. 11/891,280 filed Aug. 9, 2007, herein incorporated by reference. The term is restricted to phenomena in which the time interval between absorption and emission energy is extremely short. This fluorescence can be a positive attribute in enabling the ready detection of naphthalate containing polymers or in the development of fluorescent coatings and inks. Alternatively, the high absorption of UV radiation can produce color formation or yellowing after exposure to UV light. Although this yellowing may not impact mechanical and physical properties of the polymer, it is generally undesirable. The fluorescence, color formation, or yellowing phenomena are of concern especially in packaging of products when the product's appearance is to be as close to its natural state as desired. For example, in the packaging of foods and beverages, if food or beverages were inside a poly(ethylene-2,6-naphthalene dicarboxylate) ("PEN") container they may appear unnaturally colored.

Quenching fluorescence eliminates or reduces photon emission by providing an alternative pathway for the excited state energy, such as radiative loss (heat), or intersystem crossing to an excited triplet state. Methods to quench fluorescence in PEN have been disclosed, for example see references cited in U.S. Pat. No. 6,001,952. These examples disclose the use of o-chlorophenol to quench PEN fluorescence in chloroform solutions. Dissolving PEN in a chloroform solution to disperse a fluorescence quencher, however, is not practical since the PEN must have a low molecular weight to dissolve in the chloroform solution and only very dilute PEN solutions can be prepared.

Other compounds used to quench naphthalate fluorescence include: benzotriazoles, cyanoacrylates, benzophenones, and benzoxazinones (JP Pat. No. 08225672); cyclic imino esters or quinoxalines (EP Pat. No. 0711803); and benzylidene compounds (U.S. Pat. Nos. 4,617,374, 4,707,537, and 6,001,952). Many of these examples are disadvantageous because they require postproduction coating of fluorescent materials, show inadequate reduction in the fluorescence from fluorescent materials, or are only effective in very dilute solutions. Accordingly, there is a need for naphthalate compositions having a reduced fluorescence without deleteriously affecting the physical properties of the polymer.

The absorption of ultraviolet light by a chromophore-containing organic molecule causes the excitation of an electron in the chromophore moiety from an initially occupied, low energy orbital to a higher energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light. To photostabilize an electronically excited chromophore-containing organic molecule in order to provide sufficient UV protection, it must be returned to the ground state before it undergoes a photochemical reaction destructive to its UV absorbing capability. There are known photostabilizing sunscreen additives, such as Octocrylene, methylbenzilydene camphor, and the esters or polyesters of naphthalene dicarboxylic acid of this assignee's U.S. Pat.

Nos. 6,113,931; 6,284,916; 6,518,451; and 6,551,605, all hereby incorporated by reference, that are capable of quenching excited triplet state energy. Alkoxy crylenes, particularly methoxy crylenes, return chromophore-containing organic molecules, particularly butyl methoxydibenzoylmethane (Avobenzone), octyl methoxycinnamate (Octinoxate), and octyl salicylate (Octisalate), from both an electronically excited singlet state and excited triplet state back to their ground state, thereby photostabilizing the UV-absorbing organic molecules.

A compound known to those skilled in the art is iscotrizinol. This material sold under the trade name Unasorb ET by 3V Sigma, has the following structure and identifiers.

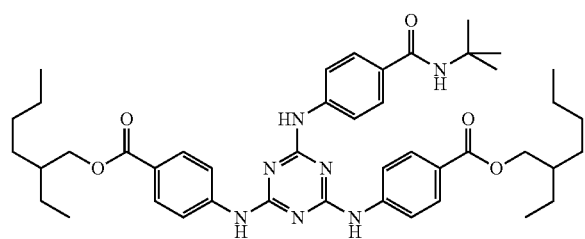 [SMILES: CCCCC(CC)COC(=O)c1ccc(Nc2nc(Nc3ccc(C(=O)NC(C)(C)C)cc3)nc(Nc3ccc(C(=O)OCC(CC)CCCC)cc3)n2)cc1]

The product has the following properties reported by 3V Sigma the manufacturer.

Chemical and Physical Characteristics

INCI Name: Ethylhexyl Triazone
IUPAC Name: 4,4'-[[6-[[4-[[(1,1-dimethylethyl)amino]carbonyl]phenyl]amino]-1,3,5-triazine-2,4-diyl]diimino]bis-,bis(2-ethylhexyl)benzoate
CAS Number: 154702-15-5
Empirical Formula: $C_{48}H_{66}N_6O_6$
Molecular Weight: 823.0
Appearance: Whitish Powder
Melt Point: <132.0
Specific Extinction:
(at 314 nm in Ethanol)

Solubility

% w/w at 25° C.

PEG-7 Glyceryl ca. 10
Cocoate:
Diisopropyl Adipate: ca. 9
C12-15 Alkyl Benzoate: ca. 4
Caprylic/Capric ca. 4
Triglyceride:
Isopropyl Palmitate: ca. 2
Mineral Oil: <1

The referenced works establish the long felt need for photostabilizing polymers that are both efficient and effective. The need is primarily in the region of UVA. It is to this area that the current invention is directed. The specific polymers of the present invention result in products, which not only ameliorate the inherent photo instability, but also form films on the surfaces to which they are applied which are water resistant and stay in place increasing effectiveness and efficiency.

All references cited are incorporated herein by reference.

THE INVENTION

Object of the Invention

The present invention has as its object a series of silicone polymers that contain a specific triazine ultraviolet photostabilizing moiety that are used to enhance the photostability of sunscreen formulations, specifically in the UVA region of the sunscreen spectrum.

An additional aspect of the present invention is to provide specific intermediates that are made in a different step then blended in the proper ratio of monoester (dicarboxylate) to diester (monocarboxylate) in order to make very specific controllable polymers that find application in sun care formulations.

Additionally, another object of the present invention is to provide specific polymers for use in sun screening applications.

Still another object of the present invention provides a process for protecting skin from the deleterious effects of the sun which comprises contacting the skin with an effective sun screening concentration of a polymer, which is produced using the current invention.

Other objects of the invention will become clear as one reads and understands the disclosure of the present invention.

All temperatures given are in degrees C., all percentages are percentages by weight and all references are incorporated herein by reference as allowed.

SUMMARY OF THE INVENTION

The present invention discloses a series of silicone polymers that contain a specific triazine ultraviolet photostabilizing group that can be used to enhance the photostability of sunscreen formulations, specifically in the UVA region of the sunscreen spectrum.

The present invention also discloses intermediate esters of a trifunctional acid of a triazine compound. These intermediates are prepared before reaction with a di hydroxyl silicone that results in the polymerization of the intermediates.

The starting trifunctional acid is 4,4',4"-((1,3,5-triazine-2,4,6-triyl)tris(azanediyl))tribenzoic acid. This well known material has a CAS number of 6355740-8. It is the fact that this material is trifunctional, and that it can be modified into partial esters that allows for a polymerization that if not made in a stepwise manner would result in a solid mass of useless polymer. The structure is:

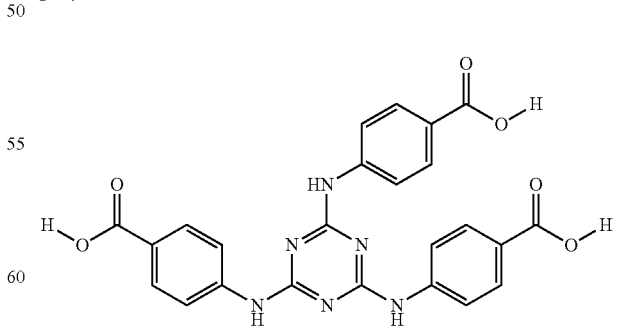

The present invention also discloses that intermediates need to be made in a preliminary step wherein the above tricarboxylic acid is reacted with an alkyl alcohol having 8-20 carbon atoms, to make either monoesters or diesters. The alkyl group can be saturated, unsaturated, or linear or branched. It has the following structure selected from the group consisting of:
(a) ROH;
(b) R—O—(CH$_2$CH$_2$—O)$_a$H;

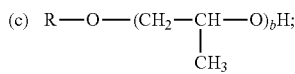

and
(d) mixtures thereof
wherein;
R is alkyl having 8 to 20 carbon atoms and is selected from the group consisting of saturated, unsaturated, linear and branched;
a is an integer ranging from 1-10;
and
b is an integer ranging from 1-10.
The resulting intermediates are as follows:
(1) Monoester (Dicarboxylate)—Chain Extender
It must be clearly understood that when one of the three carboxylic acid groups is reacted with an alcohol there remain two acid groups and the molecule has one ester functionality. Hence a monoester is by definition a dicarboxylate (since the number of ester and carboxyl groups in the intermediate must equal three. The monoester (dicarboxylate) has the following structure;

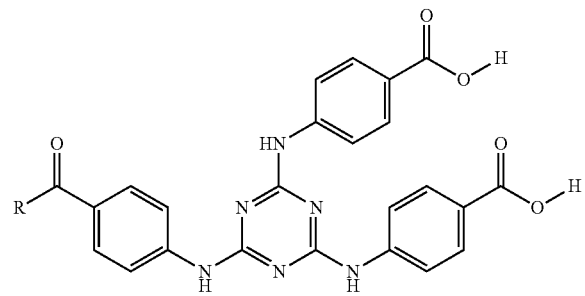

wherein;
R is selected from the group consisting of:
(a) R$^1$O—;
(b) R$^2$—O—(CH$_2$CH$_2$—O)$_a$—;

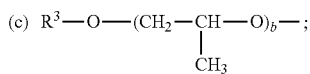

and
(d) mixtures thereof
wherein;
R$^1$, R$^2$ and R$^3$ are independently alkyl having 8 to 20 carbon atoms and is selected from the group consisting of saturated, unsaturated, linear and branched;
a is an integer ranging from 1-10;
and
b is an integer ranging from 1-10.
When there are two reactive acid groups, the molecule is referred to as difunctional such an intermediate can react with a multifunctional alcohol to make polymers. This is in stark contrast to a situation in which two of the three carboxyl groups are esterified leaving only one reaming acid group, which can only terminate the polymer chain. It is the balance between monofunctional and difunctional intermediates in the reaction mixture with the silicone diol that determines the ultimate length of the polymer that forms, and that in turn determines the functionality of the polymer viz a viz its use in formulation (2) Diester (Monocarboxylate) Chain Terminator
The chain termination diester (monocarboxylate) has the following structure:

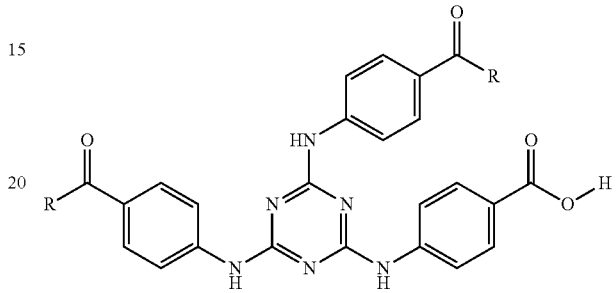 [SMILES: O=C(O)c1ccc(Nc2nc(Nc3ccc(C(=O)O)cc3)nc(Nc3ccc(C(=O)O)cc3)n2)cc1]

wherein;
R is selected from the group consisting of:
(a) R$^4$O—;
(b) R$^5$—O—(CH$_2$CH$_2$—O)$_a$—;

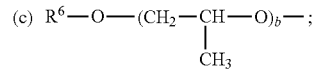

and
(d) mixtures thereof
wherein;
R$^4$, R$^5$ and R$^6$ are independently alkyl having 8 to 20 carbon atoms and is selected from the group consisting of saturated, unsaturated, linear and branched;
a is an integer ranging from 1-10;
and
b is an integer ranging from 1-10.

Molecular Design

The polymers that are the product of the current technology are what we have referred to as High Definition Polymers. By High Definition Polymers is meant a series of polyesters in which the monomer carboxy containing units are carefully controlled by (a) preparing carboxy monomers, as described herein, in a separate step (b) the selected hydroxyl monomer that is reacted with (a), and (c) the controlling the ratio of monoester (dicarboxylate) to diester (dicarboxylate) to produce the high definition polymer of the present invention.

One must clearly understand that polyesters of the present invention are prepared by the reaction of (a) a monocarboxylate (which is chain terminating), a dicarboxylate (which is chain extending) and a dihydroxy compound, in this case a silicone.

Reaction of Monocarboxylate with a Diol

The reaction of a monocarboxylate with a diol results in a diester.

$$2\ R'\!-\!\!\text{C(O))H} \ +\ \text{HO}\!-\!R''\!-\!\text{OH} \longrightarrow$$
Monocarboxylate      Diol $$R'\!-\!\text{C(O)}\!-\!\text{O}\!-\!R''\!-\!\text{O}\!-\!\text{C(O)}\!-\!R' \ +\ 2\ H_2O$$
Diester      Water The product is a diester, not a polyester.

Reaction of Monocarboxylate and Dicarboxylate with a Diol

The reaction of a monocarboxylate, and a dicarboxylate with a diol results in a polyester.

$$2\ R'\!-\!\text{C(O)OH}\ +\ x\ \text{HOC(O)}\!-\!R'''\!-\!\text{C(O)OH}\ +$$
Monocarboxylate              Dicarboxylate $$(x+1)\ \text{HO}\!-\!R''\!-\!\text{OH} \longrightarrow$$
diol $$R'\!-\![\text{C(O)}\!-\!\text{O}\!-\!R''\!-\!\text{O}\!-\!\text{C(O)}R'''\!-\!]_f\!-\!\text{C(O)}OR'\ +$$
Polyester $$(f+1)\ H_2O$$
water The value ox "f" makes the product a polyester. In the case of a diester "f" is 0, polyesters have an "f" value of at least 1. The compounds of the present invention have an "1" value of 1 to 100, and in a preferred embodiment "1" is 3-20.

Is should also be abundantly clear that R' and R" are independently selected from the group consisting on (a) alkyl having 8 to 20 carbon atoms and is selected from the group consisting of saturated, unsaturated, linear and branched;

(b) $R\!-\!O\!-\!(CH_2CH_2\!-\!O)_aH$;

(c) $R\!-\!O\!-\!(CH_2\!-\!\underset{\underset{CH_3}{|}}{CH}\!-\!O)_bH$;

and (d) mixtures thereof wherein;

a is an integer ranging from 1-10;

and b is an integer ranging from 1-10.

The location of the different functionalities on the polymer chain as either internal or external profoundly affects the solubility of the polyester.

It should also be clearly understood that the presence of tricarboxylate in the reaction mixture will result in undesired crosslinking and adversely affect the performance of the polymer in that a gel occurs. This also explains why the individual components (monocarboxylate) and (dicarboxylate) need to be prepared in a separate step rather than commixing the tricarboxylate with the other ingredients. A hopefully useless gel will occur when the tricarboxylate reacts with the difunctional silicone.

The present invention is drawn to a polyester made by the reaction of (1) a monoester (dicarboxylate) has the following structure;

wherein;

R is selected from the group consisting of:

(a) $R^1O\!-\!$;

(b) $R^2\!-\!O\!-\!(CH_2CH_2\!-\!O)_a\!-\!$;

(c) $R^3\!-\!O\!-\!(CH_2\!-\!\underset{\underset{CH_3}{|}}{CH}\!-\!O)_b\!-\!$;

and (d) mixtures thereof wherein;

$R^1$, $R^2$ and $R^3$ are independently alkyl having 8 to 20 carbon atoms and is selected from the group consisting of saturated, unsaturated, linear and branched;

a is an integer ranging from 1-10;

and b is an integer ranging from 1-10;

(2) a diester (monocarboxylate) has the following structure:

wherein;

R is selected from the group consisting of:

(a) $R^4O\!-\!$;

(b) $R^5\!-\!O\!-\!(CH_2CH_2\!-\!O)_a\!-\!$;

(c) $R^6\!-\!O\!-\!(CH_2\!-\!\underset{\underset{CH_3}{|}}{CH}\!-\!O)_b\!-\!$;

and
(d) mixtures thereof
wherein;
R⁴, R⁵ and R⁶ are independently alkyl having 8 to 20 carbon atoms and is selected from the group consisting of saturated, unsaturated, linear and branched;
a is an integer ranging from 1-10;
b is an integer ranging from 1-10;
and
(3) a silicone polymer selected from the group consisting of;

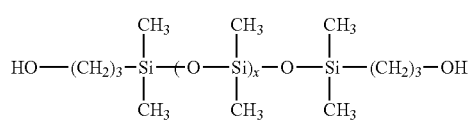

wherein x is an integer from 0 to 10;

(ii) ethoxylated

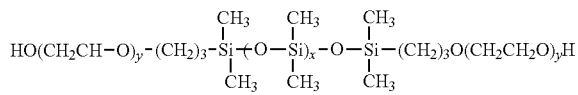

wherein y is an integer ranging from 1 to 10.

(iii) propoxylated

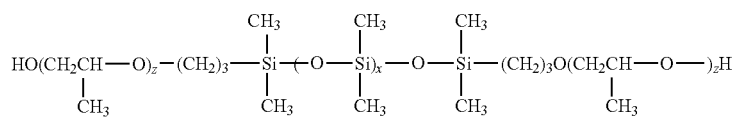

wherein z is an integer ranging from 1 to 10.
and
(iv) mixtures thereof.

The polyesters of the present invention have the following structure:

R'—[C(O)—R"—C(O)—R'"—]$_f$—C(O)—R' f is an integer ranging from 1 to 100;
R' is selected from the group consisting of;

(a) alkyl having 8 to 20 carbon atoms and is selected from the group consisting of saturated, unsaturated, linear and branched;

(b) R—O—(CH$_2$CH$_2$—O)$_a$—;

(c) R—O—(CH$_2$—CH(CH$_3$)—O)$_b$—;

and
(d) mixtures thereof;
wherein;
a is an integer ranging from 1-10;
and
b is an integer ranging from 1-10.
R" is selected from the group consisting on (a) alkyl having 8 to 20 carbon atoms and is selected from the group consisting of saturated, unsaturated, linear and branched;

(b) R—O—(CH$_2$CH$_2$—O)$_a$—;

(c) R—O—(CH$_2$—CH(CH$_3$)—O)$_b$—;

and
(d) mixtures thereof;
wherein;
a is an integer ranging from 1-10;
and
b is an integer ranging from 1-10.

R'" is selected from the group consisting of;

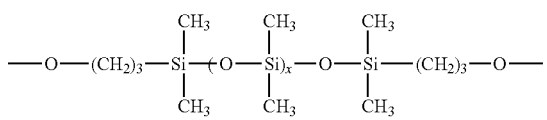

wherein x is an integer from 0 to 10;

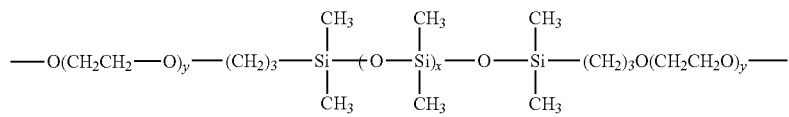

wherein y is an integer ranging from 1 to 10;

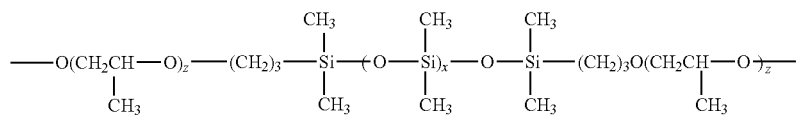

wherein z is an integer ranging from 1 to 10.
and
(iv) mixtures thereof.

PREFERRED EMBODIMENTS

In a preferred embodiment R is alkyl having 8 carbon atoms.

In a preferred embodiment R is alkyl having 10 carbon atoms.

In a preferred embodiment R is alkyl having 12 carbon atoms.

In a preferred embodiment R is alkyl having 14 carbon atoms.

In a preferred embodiment R is alkyl having 16 carbon atoms.

In a preferred embodiment R is alkyl having 18 carbon atoms.

In a preferred embodiment R is alkyl having 20 carbon atoms.

In a preferred embodiment a is 1.
In a preferred embodiment a is 2.
In a preferred embodiment a is 5.
In a preferred embodiment a is 10.
In a preferred embodiment x is 0.
In a preferred embodiment x is 2.
In a preferred embodiment x is 5.
In a preferred embodiment x is 7.
In a preferred embodiment x is 10.

Raw Materials

Example

1 Triazine Compound

The triazine compound that functions as a raw material in the preparation of the compounds of the current invention has the following structure;

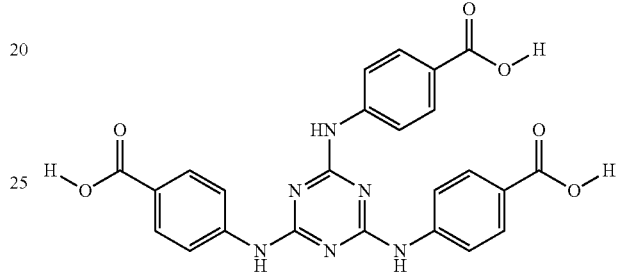

It has a CAS number of. 4,4',4"-([1,3,5]triazine-2,4,6-triylimino)tribenzoic acid (CAS #63557-10-8). It is commercially available from a variety of sources including SINO LION USA 11 Melanie Lane, Unit 4A, East Hanover, N.J. 07936.

Alcohols

The alcohols useful as raw materials have the following structure:

R—OH wherein;
R is alkyl having 8 to 20 carbon atoms and is selected from the group consisting of saturated, unsaturated, linear and branched.

They are commercially available from a variety of sources including Cognis.

| Example | Raw Material Alkyl | Fatty Alcohols MW | Name |
|---|---|---|---|---|
| 2 | C8 | C8H18O | 132 | Caprylic |
| 3 | C10 | C10H22O | 160 | Capric |
| 4 | C12 | C12H26O | 188 | Lauric |
| 5 | C14 | C14H30O | 216 | Myristic |
| 6 | C16 | C16H34O | 244 | Palmitic |
| 7 | C18 | C18H38O | 272 | Stearic |
| 8 | C20 | C20H42O | 284 | Aracadonic |
| 9 | C11— | C11H22O | 173 | Undecylenic |
| 10 | C18— | C18H36O | 270 | Oleyl |
| 11 | 2EH | C8H18O | 130 | 2 ethyl hexyl |

Ethoxylated Alcohols

The ethoxylated compounds useful as raw materials in the preparation of the polyesters of the present invention have the following structure;

R—O—(CH$_2$CH$_2$—O)$_a$H;

wherein;

R is alkyl having 8 to 20 carbon atoms and is selected from the group consisting of saturated, unsaturated, linear and branched;

a is an integer ranging from 1-10;

They are commercially available from a variety of sources including Ethox of Greenville S.C.

| Example | A | MW |
|---|---|---|
| 12 | C8 | 2 | 220 |
| 13 | C10 | 5 | 380 |
| 14 | C12 | 5 | 408 |
| 15 | C14 | 2 | 306 |
| 16 | C16 | 10 | 684 |
| 17 | C18 | 5 | 492 |
| 18 | C20 | 2 | 372 |
| 19 | C11— | 2 | 259 |
| 20 | C18— | 1 | 312 |
| 21 | 2EH | 1 | 174 |

Propoxylated Alcohols

The propoxylated compounds useful as raw materials in the preparation of the polyesters of the present invention have the following structure

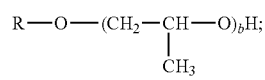

wherein;

R is alkyl having 8 to 20 carbon atoms and is selected from the group consisting of saturated, unsaturated, linear and branched;

b is an integer ranging from 1-10.

| Example | Propoxylates | b | MW |
|---|---|---|---|
| 22 | C8 | 2 | 250 |
| 23 | C10 | 5 | 455 |
| 24 | C12 | 1 | 247 |
| 25 | C14 | 10 | 806 |
| 26 | C16 | 2 | 360 |
| 27 | C18 | 1 | 331 |
| 28 | C20 | 5 | 577 |
| 29 | C11— | 3 | 348 |
| 30 | C18— | 1 | 297 |
| 31 | 2EH | 1 | 189 |

Intermediates

General Procedure

In a suitable reaction flask capable of heating the contents to 200° C. is added the specified number of grams of the specified alcohol, alcohol ethoxylate, alcohol propoxylate or mixture thereof. The reaction is heated to 170-180° C. During the heating time and once the reaction reaches around 140° C. water begins to distill off. The temperature if held between 170 and 180° C. for 5 hours, then the reaction is followed by acid value, which drops during the reaction then stabilizes.

Mono Ester Dicarboxylate

| | Alcohol Example 2-31 | | | | Product | Product % |
|---|---|---|---|---|---|---|
| Example | Example | Grams | Example | Grams | MW | Triazine |
| 32 | 2 | 132.0 | 1 | 531.0 | 645 | 80 |
| 33 | 3 | 160.0 | 1 | 531.0 | 673 | 76 |
| 34 | 4 | 188.0 | 1 | 531.0 | 701 | 73 |
| 35 | 5 | 214.0 | 1 | 531.0 | 727 | 71 |
| 36 | 6 | 244.0 | 1 | 531.0 | 757 | 68 |
| 37 | 7 | 272.0 | 1 | 531.0 | 785 | 65 |
| 38 | 8 | 284.0 | 1 | 531.0 | 797 | 64 |
| 39 | 9 | 173.0 | 1 | 531.0 | 686 | 75 |
| 40 | 10 | 270.0 | 1 | 531.0 | 783 | 66 |
| 41 | 11 | 132.0 | 1 | 531.0 | 645 | 80 |

| | Ethoxylated Alcohol | | Triazine | | Product | |
|---|---|---|---|---|---|---|
| Example | Example | Grams | Example | Grams | MW | % Triazine |
| 42 | 12 | 220.0 | 1 | 531.0 | 733 | 72 |
| 43 | 13 | 380.0 | 1 | 531.0 | 893 | 59 |
| 44 | 14 | 408.0 | 1 | 531.0 | 921 | 58 |
| 45 | 15 | 306.0 | 1 | 531.0 | 819 | 65 |
| 46 | 16 | 684.0 | 1 | 531.0 | 1197 | 44 |
| 47 | 17 | 492.0 | 1 | 531.0 | 1005 | 53 |
| 48 | 18 | 372.0 | 1 | 531.0 | 885 | 60 |
| 49 | 19 | 259.0 | 1 | 531.0 | 773 | 69 |
| 50 | 20 | 312.0 | 1 | 531.0 | 827 | 64 |
| 51 | 21 | 174.0 | 1 | 531.0 | 689 | 77 |

| | Propoxylated Alcohol | | Triazine | | Product | |
|---|---|---|---|---|---|---|
| Example | Example | Grams | Example | Grams | MW | % Triazine |
| 52 | 22 | 250.0 | 1 | 531.0 | 763 | 70 |
| 53 | 23 | 455.0 | 1 | 531.0 | 968 | 55 |
| 54 | 24 | 247.0 | 1 | 531.0 | 760 | 70 |
| 55 | 25 | 806.0 | 1 | 531.0 | 1319 | 40 |
| 56 | 26 | 360.0 | 1 | 531.0 | 873 | 61 |
| 57 | 27 | 331.0 | 1 | 531.0 | 844 | 63 |
| 58 | 28 | 577.0 | 1 | 531.0 | 1090 | 49 |
| 59 | 29 | 348.0 | 1 | 531.0 | 861 | 62 |
| 60 | 30 | 297.0 | 1 | 531.0 | 810 | 66 |
| 61 | 31 | 189.0 | 1 | 531.0 | 702 | 76 |

Diester Monocarboxylate

| | Alcohol Ex 2-31 | | Triazine | | Product | |
|---|---|---|---|---|---|---|
| Example | Example | Grams | Example | Grams | MW | % Triazine |
| 62 | 2 | 264.0 | 1 | 531.0 | 759 | 70 |
| 63 | 3 | 320.0 | 1 | 531.0 | 815 | 65 |
| 64 | 4 | 376.0 | 1 | 531.0 | 871 | 61 |
| 65 | 5 | 428.0 | 1 | 531.0 | 923 | 58 |
| 66 | 6 | 488.0 | 1 | 531.0 | 983 | 54 |
| 67 | 7 | 544.0 | 1 | 531.0 | 1039 | 51 |
| 68 | 8 | 568.0 | 1 | 531.0 | 1063 | 50 |
| 69 | 9 | 346.0 | 1 | 531.0 | 841 | 63 |
| 70 | 10 | 540.0 | 1 | 531.0 | 1035 | 51 |
| 71 | 11 | 264.0 | 1 | 531.0 | 759 | 70 |

| Ethoxylated | | | | | | |
|---|---|---|---|---|---|---|
| | Ethoxylated Alcohols | | Triazine | | Product | |
| Example | Example | Grams | Example | Grams | MW | % Triazine |
| 72 | 12 | 440.0 | 1 | 531.0 | 935 | 57 |
| 73 | 13 | 760.0 | 1 | 531.0 | 1255 | 42 |
| 74 | 14 | 816.0 | 1 | 531.0 | 1311 | 41 |
| 75 | 15 | 612.0 | 1 | 531.0 | 1107 | 48 |
| 76 | 16 | 1368.0 | 1 | 531.0 | 1863 | 29 |
| 77 | 17 | 984.0 | 1 | 531.0 | 1479 | 36 |
| 78 | 18 | 744.0 | 1 | 531.0 | 1239 | 43 |
| 79 | 19 | 518.0 | 1 | 531.0 | 1013 | 52 |
| 80 | 20 | 624.0 | 1 | 531.0 | 1119 | 47 |
| 81 | 21 | 348.0 | 1 | 531.0 | 843 | 63 |

| Propoxylated | | | | | | |
|---|---|---|---|---|---|---|
| | Propoxylated Alcohol | | Triazine | | Product | |
| Example | Example | Grams | Example | Grams | MW | % Triazine |
| 82 | 22 | 500.0 | 1 | 531.0 | 1026 | 52 |
| 83 | 23 | 910.0 | 1 | 531.0 | 1405 | 38 |
| 84 | 24 | 494.0 | 1 | 531.0 | 989 | 54 |
| 84 | 25 | 1612.0 | 1 | 531.0 | 2107 | 25 |
| 86 | 26 | 720.0 | 1 | 531.0 | 1215 | 44 |
| 87 | 27 | 662.0 | 1 | 531.0 | 1157 | 46 |
| 88 | 28 | 1154.0 | 1 | 531.0 | 1649 | 32 |
| 89 | 29 | 696.0 | 1 | 531.0 | 1191 | 45 |
| 90 | 30 | 594.0 | 1 | 531.0 | 1089 | 49 |
| 91 | 31 | 378.0 | 1 | 531.0 | 873 | 61 |

Dihydroxy Silicones

The silicone polymers useful as raw materials in the preparation of the polyesters of the present invention are selected from the group consisting of;

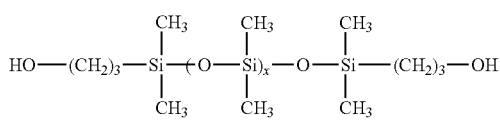

wherein x is an integer from 0 to 10;

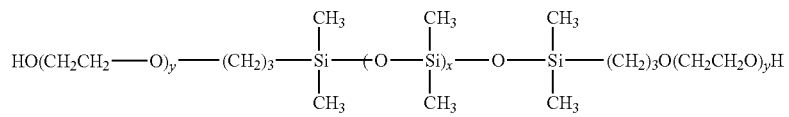

wherein y is an integer ranging from 1 to 10.

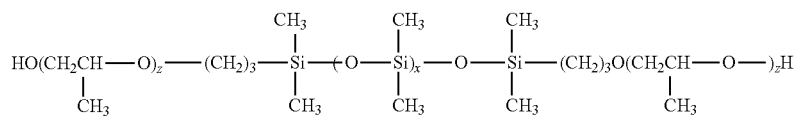

wherein z is an integer ranging from 1 to 10.

These products are commercially available from Siltech LLC of Lawrenceville, Ga. 30043.

| Example | x | MW |
|---|---|---|
| 92 | 0 | 250 |
| 93 | 2 | 398 |
| 94 | 5 | 620 |
| 95 | 7 | 768 |
| 96 | 10 | 991 |

| Example | x | Y | MW |
|---|---|---|---|
| 97 | 0 | 1 | 294 |
| 98 | 2 | 2 | 486 |
| 99 | 5 | 10 | 1060 |
| 100 | 7 | 2 | 856 |
| 101 | 10 | 1 | 1035 |

| Example | X | Z | MW |
|---|---|---|---|
| 103 | 2 | 2 | 516 |
| 104 | 5 | 10 | 1210 |
| 105 | 7 | 2 | 886 |
| 106 | 10 | 1 | 1050 |

Polymers of the Present Invention

General Procedure

In a suitable reaction flask capable of heating the contents to 200° C. is added the specified number of grams of the specified monoester, dicarboxylate, the specified number of grams of the specified diester monocarboxylate and the specified number of grams of the specified silicone diol. The reaction is heated to 170-180° C. During the heating time and once the reaction reaches around 140° C. water begins to distill off. The temperature if held between 170 and 180° C. for 5 hours, then the reaction is followed by acid value, which drops during the reaction then stabilizes.

| | Construction of Polymers of the current invention | | | | | | |
|---|---|---|---|---|---|---|---|
| | Mono carboxylate | | Di Carboxylate | | Silicone Diol | | |
| Example | Example "c" | Grams | Ex "d" | Grams | Ex | " | Grams "f" |
| 107 | 32 | 2 1290.0 | 62 | 0 0.0 | 92 | 1 | 250.0 0 |
| 108 | 33 | 2 1346.0 | 63 | 3 2445.0 | 93 | 4 | 1592.0 3 |
| 109 | 34 | 2 1402.0 | 64 | 5 4355.0 | 94 | 6 | 3720.0 5 |
| 110 | 35 | 2 1454.0 | 65 | 10 9230.0 | 95 | 11 | 8448.0 10 |
| 111 | 36 | 2 1514.0 | 66 | 12 11796.0 | 96 | 13 | 12883.0 12 |
| 112 | 37 | 2 1570.0 | 67 | 15 15585.0 | 97 | 16 | 4704.0 15 |
| 113 | 38 | 2 1594.0 | 68 | 20 21260.0 | 98 | 21 | 10206.0 20 |
| 114 | 39 | 2 1372.0 | 69 | 20 16820.0 | 99 | 21 | 22260.0 20 |
| 115 | 40 | 2 1566.0 | 70 | 15 15525.0 | 100 | 16 | 13696.0 15 |
| 116 | 41 | 2 1290.0 | 71 | 12 9108.0 | 101 | 13 | 13455.0 12 |
| 117 | 42 | 2 1466.0 | 72 | 5 4675.0 | 102 | 6 | 1854.0 5 |
| 118 | 43 | 2 1786.0 | 73 | 3 3765.0 | 103 | 4 | 2064.0 3 |
| 119 | 44 | 2 1842.0 | 74 | 0 0.0 | 104 | 1 | 1210.0 0 |
| 120 | 45 | 2 1638.0 | 75 | 0 0.0 | 105 | 1 | 886.0 0 |
| 121 | 46 | 2 2394.0 | 76 | 3 5589.0 | 106 | 4 | 4200.0 3 |
| 122 | 47 | 2 2010.0 | 77 | 5 7395.0 | 92 | 6 | 1500.0 5 |
| 123 | 48 | 2 1770.0 | 78 | 10 12390.0 | 93 | 11 | 4378.0 10 |
| 124 | 49 | 2 1546.0 | 79 | 15 15195.0 | 94 | 16 | 9920.0 15 |
| 125 | 50 | 2 1654.0 | 80 | 20 22380.0 | 95 | 21 | 16128.0 20 |
| 126 | 51 | 2 1378.0 | 81 | 5 4215.0 | 96 | 6 | 5946.0 5 |
| 127 | 52 | 2 1526.0 | 82 | 5 5130.0 | 97 | 6 | 1764.0 5 |
| 128 | 53 | 2 1936.0 | 83 | 5 7025.0 | 98 | 6 | 2916.0 5 |
| 129 | 54 | 2 1520.0 | 84 | 3 3078.0 | 99 | 4 | 4240.0 3 |
| 130 | 55 | 2 2638.0 | 84 | 3 6321.0 | 100 | 4 | 3424.0 3 |
| 131 | 56 | 2 1746.0 | 86 | 3 3078.0 | 101 | 4 | 4140.0 3 |
| 132 | 57 | 2 1688.0 | 87 | 10 11570.0 | 102 | 11 | 3399.0 10 |
| 133 | 58 | 2 2180.0 | 88 | 10 10260.0 | 103 | 11 | 5676.0 10 |
| 134 | 59 | 2 1722.0 | 89 | 20 23820.0 | 104 | 21 | 25410.0 20 |
| 135 | 60 | 2 1620.0 | 90 | 20 20520.0 | 105 | 21 | 18606.0 20 |
| 136 | 61 | 2 1404.0 | 91 | 15 13095.0 | 106 | 16 | 16800.0 15 |

The compounds are used without purification.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

I claim:

1. A polyester made by the reaction of
(1) a monoester (dicarboxylate) has the following structure;

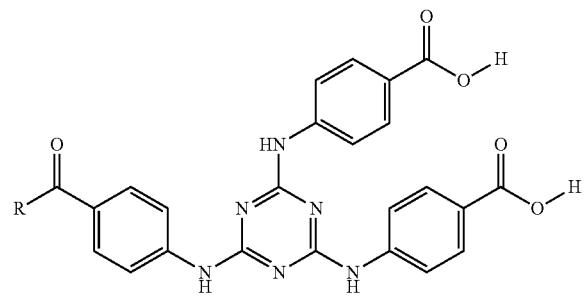

wherein;
R is selected from the group consisting of:
(a) $R^1O-$;
(b) $R^2-O-(CH_2CH_2-O)_a-$;

(c) 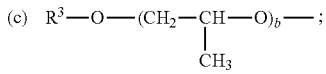

and
(d) mixtures thereof
wherein;
$R^1$, $R^2$ and $R^3$ are independently alkyl having 8 to 20 carbon atoms and is selected from the group consisting of saturated, unsaturated, linear and branched;
a is an integer ranging from 1-10;
and
b is an integer ranging from 1-10;
(2) a diester (monocarboxylate) has the following structure:

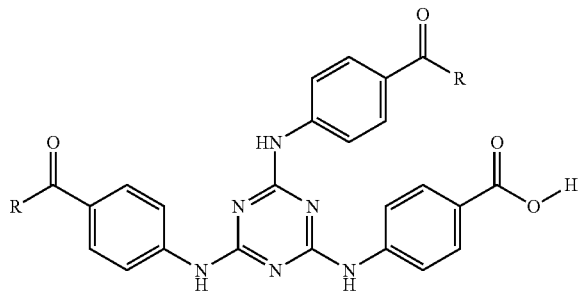

wherein;
R is selected from the group consisting of:
(a) $R^4O-$;
(b) $R^5-O-(CH_2CH_2-O)_a-$;

(c) 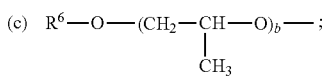

and
(d) mixtures thereof
wherein;
$R^4$, $R^5$ and $R^6$ are independently alkyl having 8 to 20 carbon atoms and is selected from the group consisting of saturated, unsaturated, linear and branched;
a is an integer ranging from 1-10;
b is an integer ranging from 1-10;
and
(3) a silicone polymer selected from the group consisting of;
(i)

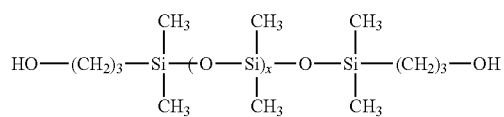

wherein x is an integer from 0 to 10;

(ii) ethoxylated

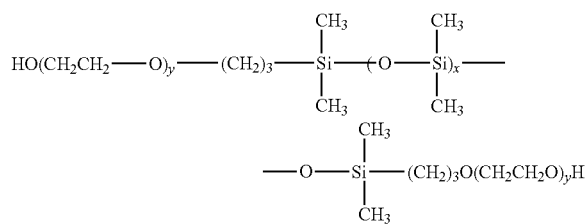

wherein y is an integer ranging from 1 to 10;
(iii) propoxylated

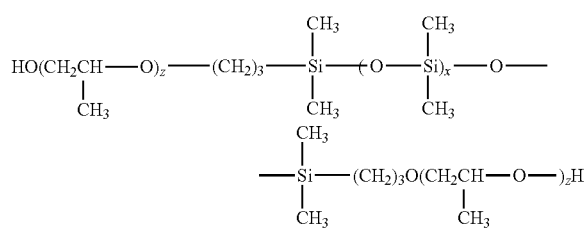

wherein z is an integer ranging from 1 to 10;
and
(iv) mixtures thereof.

2. The polyester of claim 1 wherein $R^1$ $R^2$ and $R^3$ are alkyl having 8 carbon atoms.
3. The polyester of claim 1 wherein $R^1$ $R^2$ and $R^3$ are alkyl having 10 carbon atoms.
4. The polyester of claim 1 wherein $R^1$ $R^2$ and $R^3$ are alkyl having 12 carbon atoms.
5. The polyester of claim 1 wherein $R^1$ $R^2$ and $R^3$ are alkyl having 14 carbon atoms.
6. The polyester of claim 1 wherein $R^1$ $R^2$ and $R^3$ are alkyl having 16 carbon atoms.
7. The polyester of claim 1 wherein $R^1$ $R^2$ and $R^3$ are alkyl having 18 carbon atoms.
8. The polyester of claim 1 wherein $R^1$ $R^2$ and $R^3$ are alkyl having 20 carbon atoms.
9. The polyester of claim 1 wherein a is 1.
10. The polyester of claim 1 wherein a is 2.
11. The polyester of claim 1 wherein a is 5.
12. The polyester of claim 1 wherein a is 10.
13. The polyester of claim 1 wherein x is 0.
14. The polyester of claim 1 wherein x is 2.
15. The polyester of claim 1 wherein x is 5.
16. The polyester of claim 1 wherein x is 7.
17. The polyester of claim 1 wherein x is 10.

* * * * *